US009858631B2

(12) United States Patent
Farr et al.

(10) Patent No.: US 9,858,631 B2
(45) Date of Patent: Jan. 2, 2018

(54) PERSONAL MEDICAL INFORMATION STORAGE DEVICE AND SYSTEM

(71) Applicant: Intelligent ID Solutions, LLC, Bountiful, UT (US)

(72) Inventors: Jason E. Farr, Farmington, UT (US); John G Coram, Alpine, UT (US); Greg T Meyers, Providence, UT (US)

(73) Assignee: Intelligent ID Solutions, LLC, Bountiful (*) Notice: Subject to any disclaimer, the term of this patent is extended or adjusted under 35 U.S.C. 154(b) by 222 days.

(21) Appl. No.: 13/660,890

(22) Filed: Oct. 25, 2012

(65) Prior Publication Data

US 2014/0122118 A1   May 1, 2014

(51) Int. Cl.
*G06Q 50/24* (2012.01)
*G06Q 30/02* (2012.01)

(52) U.S. Cl.
CPC ......... *G06Q 50/24* (2013.01); *G06Q 30/0251* (2013.01)

(58) Field of Classification Search
CPC ...................................................... G06F 21/81
See application file for complete search history.

(56) References Cited

U.S. PATENT DOCUMENTS 5,337,290 A   8/1994   Ventimiglia et al.
5,995,077 A   11/1999  Wilcox et al.
6,985,870 B2  1/2006   Martucci et al.
7,006,408 B2  2/2006   Chen
7,778,848 B1  8/2010   Reeves
(Continued)

FOREIGN PATENT DOCUMENTS

CN   2904054 Y     5/2007
CN   201019738 Y   2/2008
(Continued)

OTHER PUBLICATIONS

Electronic Medical ID Bracelet Size X Small—Emergency 256 MB Flash Drive USB Memory Wristband Stores Health History for English & Spanish / Espanol ; downloaded Aug. 13, 2012 from http://www.amazon.com/Electronic-Medical-Bracelet-Size-Small/dp/B004ZXTP16.
(Continued)

*Primary Examiner* — Robert Morgan
*Assistant Examiner* — Kristine Rapillo
(74) *Attorney, Agent, or Firm* — Loza & Loza, LLP; Tyler J. Barrett

(57) ABSTRACT

A subscription-based personal medical information storage device comprises a data storage unit comprising a computer readable storage medium configured to store medical and non-medical information of a user, and facilitate the retrieval of medical and non-medical information of the user from a remote medical information storage device. The data storage unit is configured to automatically run an authentication routine upon connection with the general purpose computing device to confirm that the personal medical information storage device is neither lost nor stolen before granting access thereto. A communication module is configured to facilitate a communication connection with the remote medical information storage device, and wherein the remote medical information storage device comprises an advertisement module.

17 Claims, 12 Drawing Sheets

(56) References Cited

U.S. PATENT DOCUMENTS

| | | | |
|---|---|---|---|
| 7,865,735 B2 | 1/2011 | Yiachos | |
| 8,088,043 B2 | 1/2012 | Andren et al. | |
| 8,180,654 B2 | 5/2012 | Berkman et al. | |
| 8,812,860 B1* | 8/2014 | Bray | 713/182 |
| 2004/0057340 A1* | 3/2004 | Charles-Erickson et al. | 368/10 |
| 2006/0074718 A1* | 4/2006 | Fucci et al. | 705/3 |
| 2006/0080137 A1 | 4/2006 | Chambers et al. | |
| 2007/0078688 A1 | 4/2007 | Bischof et al. | |
| 2008/0005059 A1 | 1/2008 | Colang et al. | |
| 2008/0016738 A1 | 1/2008 | Talbott | |
| 2008/0021739 A1 | 1/2008 | Brock | |
| 2008/0027752 A1 | 1/2008 | Phan et al. | |
| 2008/0059236 A1 | 3/2008 | Cartier | |
| 2008/0071577 A1* | 3/2008 | Highley | 705/3 |
| 2008/0268924 A1* | 10/2008 | Chang | 455/575.5 |
| 2008/0291744 A1 | 11/2008 | Hasvold | |
| 2008/0319799 A1 | 12/2008 | Knowlton | |
| 2009/0030729 A1 | 1/2009 | Doyle | |
| 2009/0271221 A1 | 10/2009 | Aridi et al. | |
| 2009/0281836 A1 | 11/2009 | Velarde | |
| 2012/0069511 A1 | 3/2012 | Azera | |
| 2013/0091012 A1* | 4/2013 | Liberty | 705/14.51 |

FOREIGN PATENT DOCUMENTS

| | | | | |
|---|---|---|---|---|
| CN | 102183887 A | 9/2011 | | |
| GB | 2431858 A | 5/2007 | | |
| GR | 20100100228 | 6/2011 | | |
| JP | 2003140771 | 5/2003 | | |
| MX | NL06000016 A | 9/2007 | | |
| WO | WO2010109367 A2 | 9/2010 | | |
| WO | WO 2013/044312 | * | 4/2013 | G06F 21/81 |

OTHER PUBLICATIONS

"HealthID Profile" Downloaded Aug. 13, 2012 at http://www.healthidprofile.com/Account/LogOn.

"Medical Alert Hologram" date downloaded Aug. 13, 2012 from http://www.universalmedicaldata.com/shop/category/all-0.html?keywords=USB&category=17&Submit=Search.

Medical Alert Jewelry USB flash drive downloaded on Aug. 13, 2012 from http://www.alibaba.com/product-gs/356053844/Medical_Alert_Jewelry_USB_flash_drive.html.

"Medical Alert USB Flash Drive Silicone Bracelet" Downloaded Aug. 13, 2012 at http://www.amazon.com/Medical-Alert-Flash-Silicone-Bracelet/dp/B0044YQ6K6/ref=pd_sxp_grid_pt_0_2.

New! Black MedicAlert® Sports Band downloaded on Aug. 13, 2012 from http://www.medicalert.org/shop/emergency-medical-id/sports-band/detail/A797.htm?n=NEW!+Black+MedicAlert%C2%AE+Sports+Band.

"Personalized Care Bracelets" downloaded Aug. 13, 2012 at http://medicalhistorybracelet.com/.

Stylish Medical ID Bracelet with USB downloaded on Aug. 13, 2012 from http://www.amazon.com/Stylish-Medical-ID-Bracelet-USB/dp/B006AUVYFY/ref=pd_cp_pc_3.

USB Medical ID Bracelet; http://www.alibaba.com/product-gs/595910300/usb_medical_id_bracelet.html.

"Care Memory Band" Downloaded Aug. 13, 2012 from http://www.phc-online.com/Medical_Alert_Bracelet_p/care-memory-band.htm.

* cited by examiner

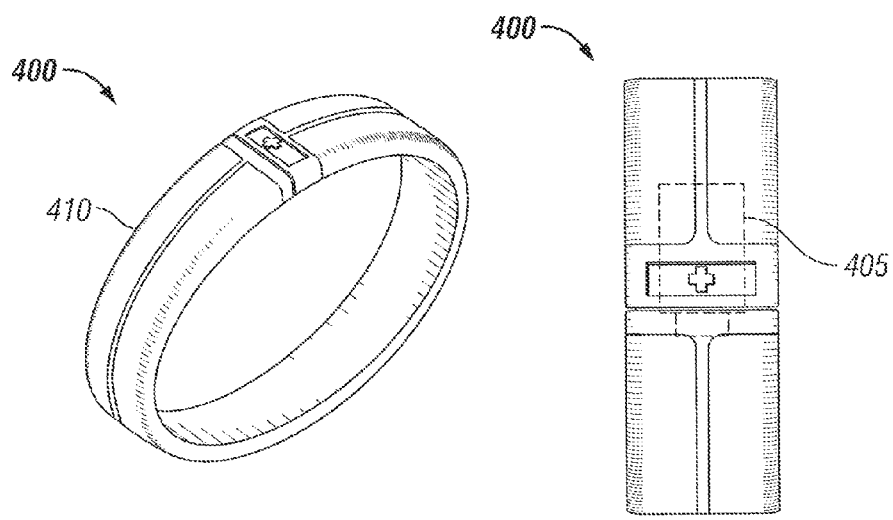
FIG. 4A
FIG. 4B
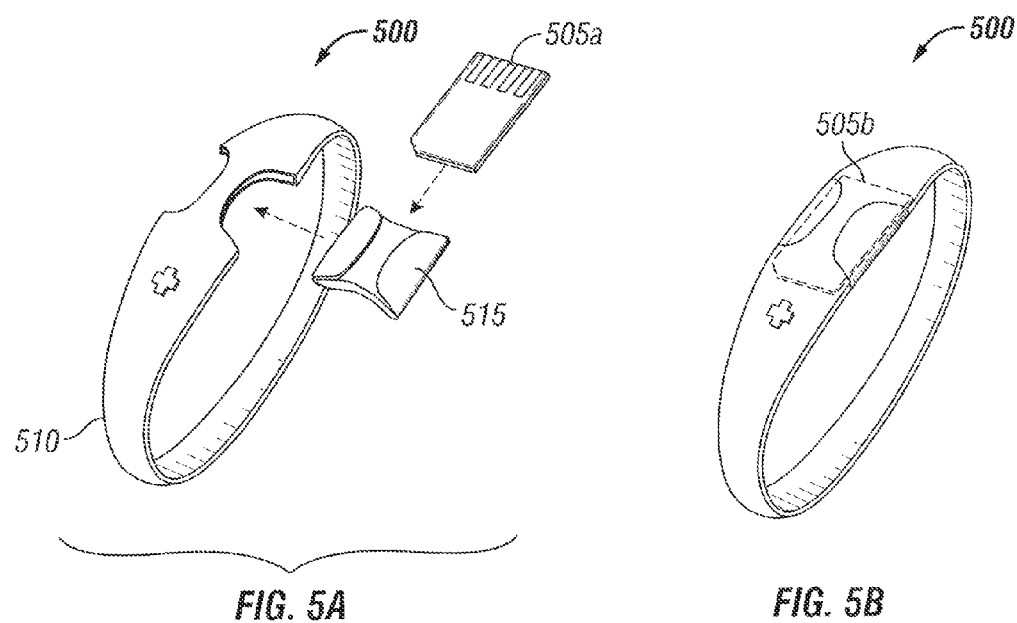
FIG. 5A
FIG. 5B

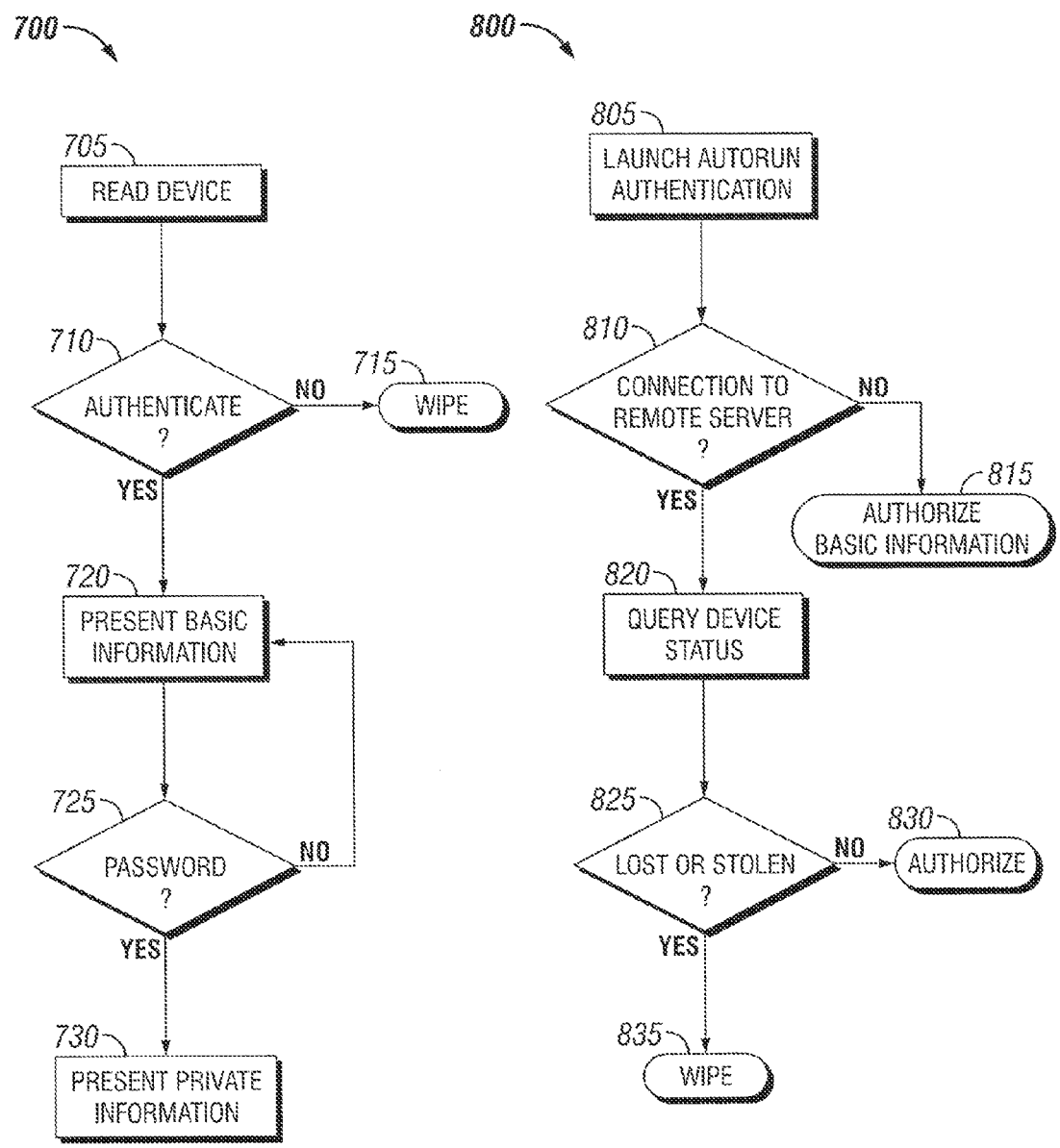

FIG. 15

PERSONAL MEDICAL INFORMATION STORAGE DEVICE AND SYSTEM

BACKGROUND

Emergency responders often encounter the challenge of administering aid to unconscious patients, or patients that are not lucid. Such situations present challenges related to unknown allergies, existing conditions, and medications already in the patient's system, among other things.

Another challenge facing emergency responders is ensuring that information provided is up-to-date and accurate. For instance, a number of medical information storage devices exist on the market, but are often of little use to emergency responders because the information contained thereon may be woefully out-of-date.

Physicians, on the other hand, are forced to deal with the challenge of collecting vast amounts of information from patients prior to appointments and in conjunction with treatments. For instance, prior to a first appointment with a physician, patients may be asked to spend over a quarter of an hour filling out paper work that they may have filled out before and may be asked to fill out again.

Users often face the challenge of storing important medical (and non-medical) documents in one central, secure location that may be readily accessed when needed, such as at a doctor's appointment, among other things. Additionally, such important medical and non-medical information is invariably not accessible when it is needed most.

A large number of potential solutions to the above problems have been proposed, but one of the largest challenges for companies seeking to market a product is covering operating costs. For example, the infrastructure to store and transmit large amounts of medical data may be expensive to set up and maintain.

SUMMARY

There is a need for a device and a system configured to store medical and non-medical information in a secure, centralized location. There is also a need to create a device and system that may permit physicians to quickly and efficiently share information, and for patients to transfer information to different physicians. There is also a need for a system and device configured to ensure that information stored thereon is up-to-date and current. Finally, there is a need for a device and system that offers financing options that may make the manufacture, marketing, sale, and operation thereof financially realizable.

A subscription-based personal medical information storage device includes a data storage unit having a computer readable storage medium configured to store medical and non-medical information of a user, and facilitate the retrieval of medical and non-medical information of the user from a remote medical information storage device. The data storage unit is configured to be read by a general purpose computing device, and the data storage unit is configured to automatically run an authentication routine upon connection with the general purpose computing device to confirm that the personal medical information storage device is neither lost nor stolen before granting access thereto. The data storage unit further includes a communication module configured to facilitate a communication connection with the remote medical information storage device, and wherein the remote medical information storage device comprises an advertisement module configured to: (a) prompt a user for authorization to parse the medical information of the user to provide personalized advertisements and recommendations in exchange for a reduced cost subscription plan, (b) upon reception of user authorization, parse the medical information of the user to facilitate the identification of relevant advertisements, (c) present the user with at least one relevant advertisement, and (d) offer a reduced cost subscription plan or service credit to the user.

A medical information storage system includes a medical information storage server configured to store medical and non-medical information from users of the medical information storage system, a personal medical information storage device configured to exchange information with the medical information storage server and to store medical and non-medical information in a computer readable storage medium. The medical information storage server includes an advertisement module configured to parse medical and non-medical information stored on the medical information storage server and the personal medical information storage device, and to facilitate the identification of at least one relevant advertisement or recommendation for a user based upon the medical and non-medical information of the user. The medical information storage server also includes communication module configured to communicate the at least one relevant advertisement or recommendation to the user.

A personal medical information storage device includes a computer readable storage medium configured to store both medical and non-medical information. An authentication module is stored on the computer readable storage medium. The authentication module is configured to communicate with a remote medical information storage device and verify that the personal medical information storage device has not been reported (a) lost, or (b) stolen, and wherein the authentication module is configured to erase the medical and non-medical information of the computer readable storage medium upon a determination that the medical information storage device has been lost or stolen. The personal medical information storage device also includes a physician note module stored on the computer readable storage medium and includes an encrypted physician notes field, an encrypted physician files field for images and PDFs, a save functionality configured to restrict access to the encrypted physician notes field and the encrypted physician files field to read-only access and delete-only access, and a form module configured to store a plurality of doctor-specific forms for downloading on a general purpose computing device.

BRIEF DESCRIPTION OF THE DRAWINGS

FIGS. 4a and 4b are an illustration of a personal medical information storage device.

FIGS. 5a and 5b are an illustration of another personal medical information storage device.

FIG. 7 illustrates a method of using a personal medical information storage device.

FIG. 8 illustrates a method of authenticating a personal medical information storage device.

FIG. 15 is an example of a screen shot presenting physician notes as saved to a personal medical information storage system.

Like reference numbers and designations in the various drawings indicate like elements.

DETAILED DESCRIPTION

In the following detailed description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that various changes may be made without departing from the spirit and scope of the present invention. The following detailed description is, therefore, not to be taken in a limiting sense.

Figure 1:
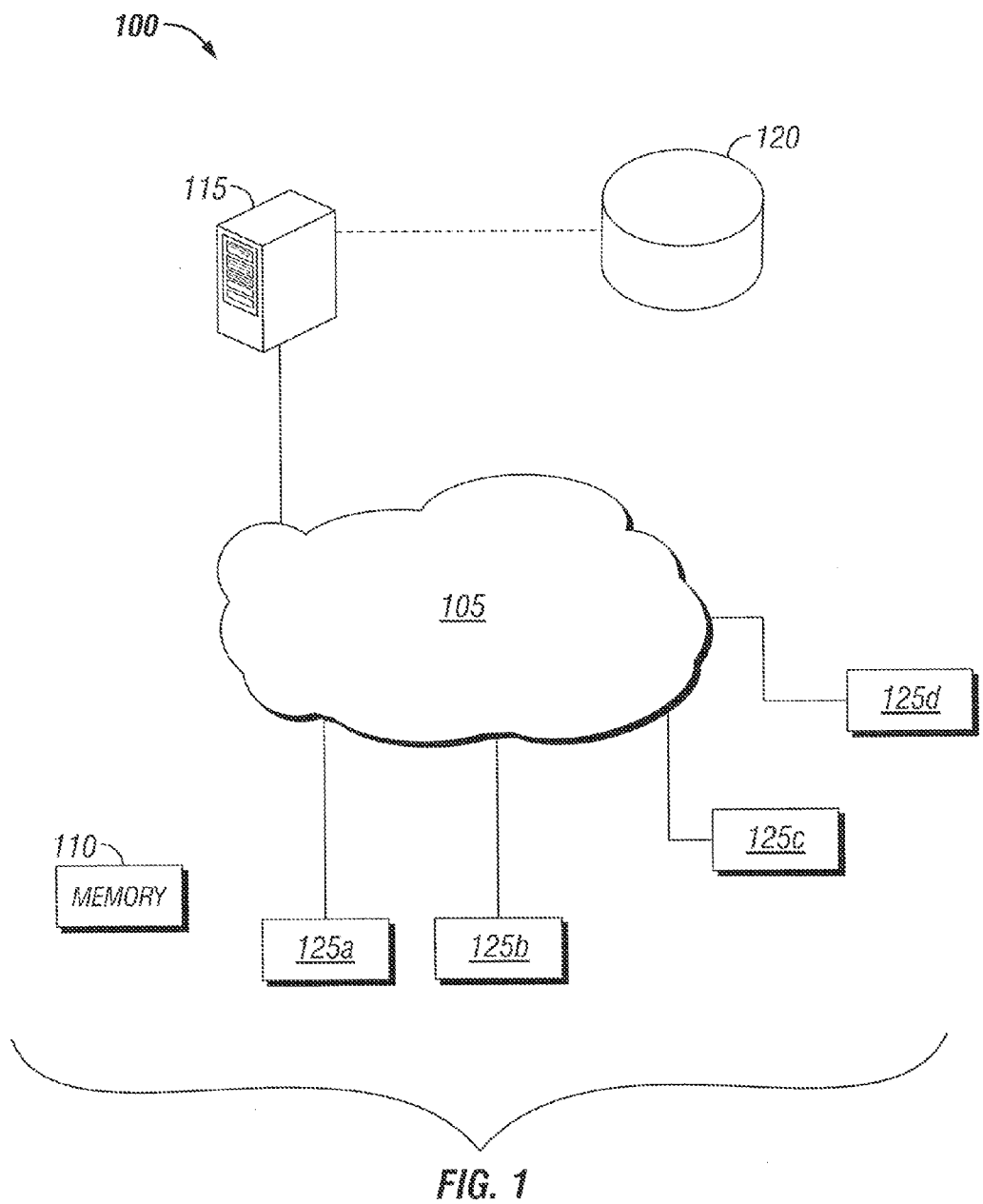
FIG. 1 is a representation of personal medical information storage system.

FIG. 1 illustrates a medical information storage system 100 comprising a network 105 connecting client devices 125a-125d to a network interface server 115. A personal medical information storage device 110 may be connected to a client device 125a-125d. Personal medical information may be stored on personal medical information storage device 110 or remotely in a database 120. Database 120 may be stored on network interface server 115, or may be stored on a separate server or servers.

Network 105 may be any form of network such as, for example, a private IP network, a WAN, a LAN, an intranet, or the Internet, among other things. Of course, any other number of possible network embodiments are contemplated by the present disclosure. Each respective connection to network 105 of client devices 125a-125d and network interface server 115 may be any form of wired or wireless connection. For instance, client device 125a may be connected to network 105 via a wired connection, such as a DSL, cable broadband, or dial-up connection, or a wireless connection such as a GSM, Wi-Fi, or satellite connection, among other things. Analogously, network interface server 115 may be connected to network 105 via a wired or wireless connection.

Network interface server 115 may be any number of appropriate servers. For instance, in one embodiment, network interface server 115 may be an http server. FIG. 1 illustrates a handful of client devices 125a-125d that represent various possible computing devices that may be used in connection with personal medical information storage device 110 according to the present disclosure. For instance, client device 125a (a desktop computer) represents a PC, Mac, Linux or other appropriate client device; client device 125b represents a laptop computer or possibly a netbook; client device 125c represents a tablet device such as an iPad®; and client device 125d represents a PDA or smartphone device. Client devices 125a-125d may comprise USB, mini-USB, card reader, or other I/O connections that may facilitate connecting personal medical information storage device 110 thereto.

In operation, personal medical information storage device 110 may be connected to a client device 125a-125d to facilitate personal medical information storage and entry. For instance, a user may connect personal medical information storage device 110 into client device 125a, and may thereafter input personal medical information to be saved and stored on the personal medical information storage device 110. Thereafter, personal medical information storage device 110 may be carried on or with the user and may be relied upon to assist in transferring sensitive and essential personal medical information should the need arise. For instance, the user may have a doctor's appointment or may be injured in a car accident. In the former case, the user may allow an assistant at the doctor's office to access the data stored on personal medical information storage device 110 to facilitate the transfer of necessary information that may be used to provide efficient service and care. In the case of a car accident, emergency responders may be able to read the data stored on personal medical information storage device 110 to assist the user. Clearly, these two examples are intended to facilitate understanding and are not to be interpreted restrictively. Indeed, any number of possible uses are contemplated by the present disclosure.

In one embodiment, upon connection of personal medical information storage device 110 with client device 125a or 125b (for example), an autorun routine contained on personal medical information storage device 110 may run and verify a connection with network interface server 115 and database 120 (or attempt to establish a connection thereto), exchange information, and verify that personal medical information storage device 110 is not lost or stolen, for example. In another embodiment, the personal medical information on personal medical information storage device 110 may be compared with the personal medical information in database 120 to verify that the information is up-to-date. For instance, if the information on personal medical information storage device 110 is determined to be out-of-date (as compared to the information in database 120), then the relevant information may be transferred to personal medical information storage device 110, or vice versa.

In yet another embodiment, once personal medical information storage device 110 is connected to a client device, such as client device 125a, personal medical information storage device 110 or network interface server 115 may determine that the client device 125a is that of a participating service provider, and may apply a predetermined provider layer in order to facilitate and standardize the presentation of the user's medical information. For instance, a participating service provider may have a corresponding user interface layer that automatically formats the user's medical information into the provider's preferred intake form, among other things. The provider layer may also facilitate data display and entry to enable the provider and his or her staff to update a personal medical information storage device 110 with any number of relevant data and information such as, for example, X-rays, diagnoses, medication histories, allergies, appointments, and physician notes, among other things.

In another embodiment, personal medical information storage device 110 may be a card with a URL and a member number that, rather than requiring a provider to insert personal medical information storage device 110 directly into a client device 125a, may permit the service provider to rapidly and easily access a remote website with the user's personal medical information stored thereon. For instance, in one example, if a user is injured and unconscious or not otherwise lucid, emergency responders may be able to enter a URL into their client device (such as client devices 125a-125d) and enter the user's ID number to retrieve a list of allergies and vital personal medical information to facilitate their tasks. Alternatively, personal medical information storage device 110 may comprise a bar code or QR Code to be scanned and quickly take emergency responders to a page displaying the user's basic personal medical information.

Figure 2:
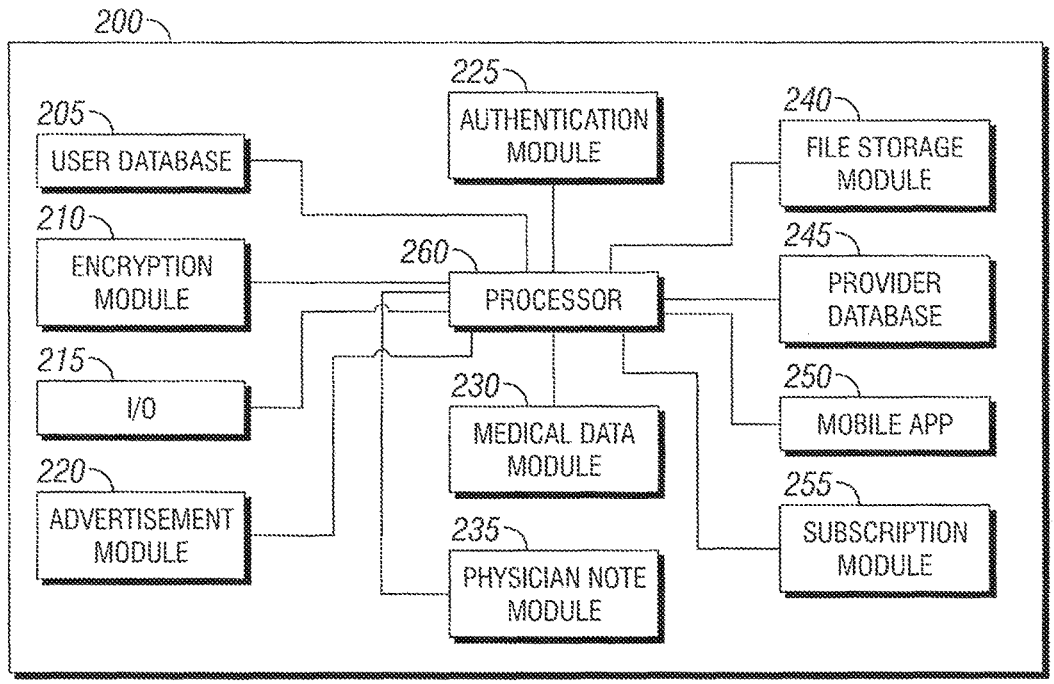
FIG. 2 is a block diagram representation of a remote medical information storage device.

FIG. 2 is a block diagram representation of a remote medical information storage device 200. Remote medical information storage device 200 comprises a user database 205, an encryption module 210, an I/O module 215, an advertisement module 220, an authentication module 225, a medical data module 230, a physician note module 235, a file storage module 240, a provider database 245, a mobile app module 250, a subscription module 255, and a processor 260. Each module 205-255 of remote medical information storage device 200 is connected to processor 260 in order to facilitate access to and use thereof.

Remote medical information storage device 200 may be a server or any number of servers that store medical information remotely. User database 205 may be a single database or any number of databases configured to store user data including, but not limited to, user names, ID numbers, passwords, and medical and non-medical information, among other things. User database 205 may reside on a single remote medical information storage device 200, across multiple remote medical information storage devices 200, or even multiple remote computers (e.g., for instance, the password database may reside on a company server and the remaining modules on a health provider's server). User database 205 may be connected to a processor 260 for data processing.

Encryption module 210 represents any module related to data encryption. For instance, it may be beneficial to encrypt data as it is transferred between network interface server 115 and client devices 125a-125d. Encryption may also be beneficial for data stored on personal medical information storage device 110 or in database 120. For example, unencrypted data may be accessed and stolen or read, while encrypting data may serve as an additional layer of protection to avoid data theft. Encryption module 210 may be connected to processor 260. Data may be transferred between modules, such as between user database 205 and encryption module 210, via processor 260.

I/O module 215 represents any module configured to control the I/O interface of remote medical information storage device 200. I/O module 215 is connected to processor 260 to enable the communication of modules, among other things. For instance, I/O module 215 may enable communication of data with user database 205 and a client device 125a, via processor 260. Generally speaking, I/O module 215 operates consistent with a general understanding of the term.

Advertisement module 220 represents a module configured to enable product advertisements and recommendations. Advertisement module 220 is connected to processor 260 and is therefore in communication with the other modules of remote medical information storage device 200. For instance, advertisement module 220 may exchange data with user database 205 in order to assess a given user's relevant medical needs and to propose relevant advertisements and recommendations. In one example, a diabetic may receive an advertisement related to a new insulin test. In another example, a user with high blood pressure may be informed of a new blood pressure medication. In yet another embodiment, users may receive advertisements or recommendations directly from their health care providers. For instance, a physician may desire to remind a patient to seek a refill after a predetermined period of time has elapsed, and therefore, advertisement module 220 may be configured to facilitate such reminders. Of course, as may be readily from the present disclosure, any number of possible uses of advertisement module 220 are contemplated by the present disclosure. The preceding examples are provided as a few of the possibilities intended.

Authentication module 225 represents a module configured to authenticate a personal medical information storage device 110. For instance, when a personal medical information storage device 110 is read by a client device 125a, prior to allowing access to the personal medical information storage device 110 remote medical information storage device 200 may verify that the personal medical information storage device 110 has not been reported lost or stolen. The authentication module 225 may authenticate using any suitable authentications means. For instance, an authentication script or routine in any possible form may be employed and is contemplated by the present disclosure. As used herein, authentication routine refers to any possible form of authentication used to verify the status of a personal medical information storage device 110. In one embodiment, if it is determined that the personal medical information storage device 200 has been reported lost or stolen, authentication module 225 may transmit a command to wipe or erase the data stored on the personal medical information storage device 200. Otherwise, authentication module 225 may grant access to the information contained on personal medical information storage device 110.

Medical data module 230 represents a module configured to store medical data. In some cases, a user's medical data may be stored in user database 205; however, in other cases it may be desirable to store medical data in a dedicated medical data module 230. Medical data module 230 may also be used to store provider information such as provider-specific medical forms. Medical data module 230 is connected to processor 260 in order to enable communication between modules. In one embodiment, medical information may be transferred from I/O module 215 to medical data module 230 via processor 260.

Physician note module 235 represents a module configured to store physician notes. For example, a physician may draft and store a note regarding, for instance, a diagnosis to facilitate the exchange of information with other physicians. In one embodiment, physician note module 235 may be configured such that once a physician saves a note, it may not be edited. Physician note module 235 may be configured to encrypt and otherwise store physician notes with protection. Physician note module 235 may protect sensitive information by any suitable means. For instance, in one example, physician note module 235 may comprise UNIX-like permissions and may only grant read permissions. Alternatively, physician note module 235 may also permit the deletion, but deletion only, of physician notes. In another example, physician note module 235 may comprise Microsoft or IBM DOS variant attributes to restrict access to read-only or delete-only access. Of course, the preceding are merely illustrative examples not intended to be taken in a limiting sense.

File storage module 240 represents a module configured to store user files such as, for example, images, and PDFs, among other things. For instance, a user may desire to store a birth certificate, copies of vaccination records, or non-medical information such as copies of insurance policies, lists of valuables, and living wills, among other things.

Provider database module 245 represents a module related to provider-specific information. In one embodiment, a provider may pre-load predetermined information and files such as, for example, specific forms and pamphlets. Provider database module 245 may also comprise provider layers configured to apply a standardized layer specific to a given provider. Provider database module 245 may communicate with other modules of remote medical information storage device 200.

Mobile app module 250 represents a module configured to present the different modules and information stored in remote medical information storage device 200 in a format for small screens such as for smartphones. For instance, remote medical information storage device 200 may determine that client device 125d has made a request for information, may determine that client device 125d is a smartphone, and may direct all communications through mobile app module 250 to ensure that the data appears as desired.

Subscription module 255 represents a module configured to track and monitor a user's subscription information. For instance, in one embodiment, when a user connects personal medical information storage device 110 to client device 125a, remote medical information storage device 200 may send a request to subscription module 255 to confirm that the user has an account in good standing. In this embodiment, a user with outstanding account issues may be prompted to take action and may be given limited access (or no access at all) to services related to his or her account. Otherwise, the user may be given access to his or her data as displayed by default. In one embodiment, a subscription may be required to access some or all of the functionality of the personal medical information storage device 110.

Figure 3:
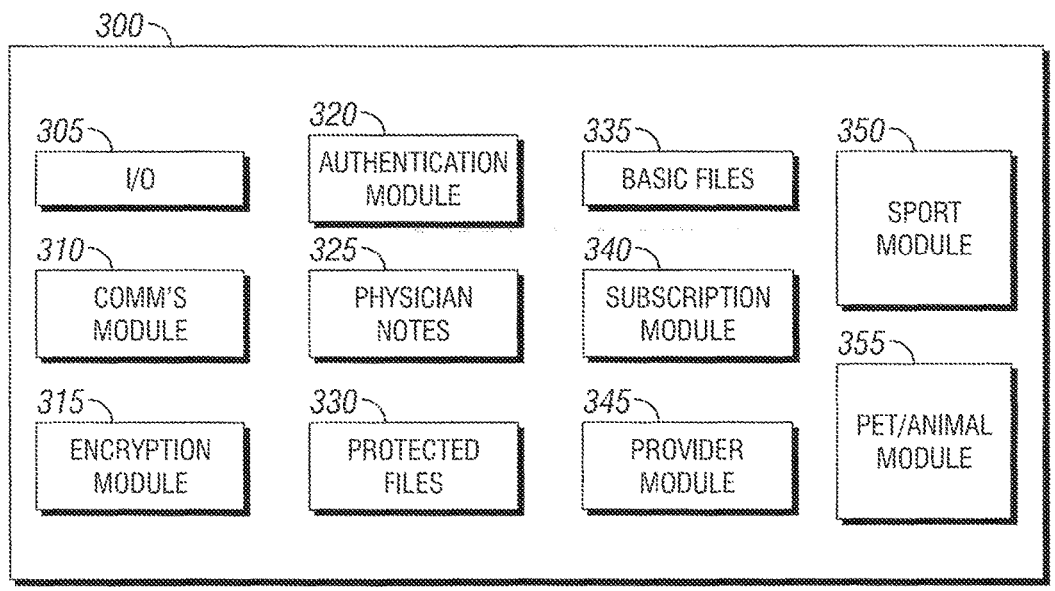
FIG. 3 is a block diagram representation of a personal medical information storage device.

FIG. 3 shows a block diagram representation of a personal medical information storage device 300. Personal medical information storage device 300 may comprise a plurality of modules including, an I/O module 305, a communications module 310, an encryption module 315, an authentication module 320, a physician notes module 325, a protected files module 330, a basic files module 335, a subscription module 340, a provider module 345, a sport module 350, and a pet/animal module 355, among other things. Many of the modules have been discussed above in relation to remote medical information storage device 200. The modules may be stored on a data storage unit, or memory unit, of personal medical information storage device 300. For instance, in one embodiment, personal medical information storage device 300 comprises an electronic, magnetic, or resistive memory device.

Communications module 310 represents a module configured to enable the communication of data from personal medical information storage device 300 and remote medical information storage device 200. In one embodiment, communications module 310 may facilitate the communication between a client device 125a and a remote interface server 115. As used herein, a communication connection is any connection configured to enable the transmission and reception of data between a personal medical information storage device 300, via a client device 125a, and a remote medical information storage device 200, and may be established by communications module 310. Protected files module 330 represents a module configured to store and facilitate access to files that have been identified as "protected" by the user. For instance, in one embodiment sensitive personal information, such as social security numbers, medical and medication histories, birth certificates, among other things, may be specially identified as "protected" and may only be accessed by password. On the other hand, in this embodiment, non-protected files such as vaccination records or any other files that the user wishes to be accessed without having to enter a password may be stored in a basic files module 335.

Sport module 350 represents a module configured to store sport-specific information. For example, in one embodiment sport module 350 is configured to store data related to a user's exercise routine including histories, performance, and goals, among other things. Pet/animal module 355 may be configured to store pet/animal-specific information such as, for example, medical history. In one embodiment, pet or animal information may be stored on the pet owner's device. Alternatively, pet or animal information may be stored on a personal medical information storage device 300 stored on, for instance, a collar.

In operation, the different modules of personal medical information storage device 300 may work in concert with remote medical information storage device 200, and with corresponding modules thereof, in order to facilitate the exchange of medical information, to ensure that a user's information is up-to-date, and to protect user information against theft and loss. In one example, personal medical information storage device 300 may be connected to a client device 125a, following which, the authentication module 320 operates to communicate with the user database 205 and processor 260 of a remote medical information storage device 200. Once personal medical information storage device 300 receives a confirmation of authentication, then client device 125a may display information from basic files 335, from the physician notes 325, and protected files 330, among other things.

Personal medical information storage device 300 may include other modules. For instance, it may also include an update module configured to store, organize, and detect triggering events for prompting a user to update his or her medical or non-medical information stored on personal medical information storage device 300 or remote medical information storage device 200. In one embodiment, the update module may store a plurality of triggering events including but not limited to (a) time elapsed since previous data entry, (b) life events, such as a birth or marriage, (c) an upcoming appointment with a provider, or (d) a request from a service provider, among other things. For instance, the update module may be configured to alert a user to update personal information if, for example, a predetermined amount of time elapses since the previous data entry. In one embodiment, the predetermined amount of time may be three months; or it may be one year. In another embodiment, the update module may be configured to prompt a user to update medical or non-medical information at periods of the year where there may typically be changes, such as in September or October, after the beginning of a new school year.

In one embodiment, the update module may prompt a user to update medical and non-medical information prior to an upcoming appointment with a provider or at the request of a provider. For example, the update module may receive a communication from a remote medical information storage device 200 indicating an upcoming appointment with a provider, and in response, the update module may prompt the user to enter updated medical and non-medical information via, inter alia, a client device 125a. Alternatively, a provider may transmit a request, via remote medical information storage device 200, to the update module to prompt a user to update medical or non-medical information.

The update module may also be configured to detect the arrival or pending arrival of one of the triggering events. Once, a triggering event is detected, the update module may prompt the user, via a pop-up on a client device 125a, a phone call, or any other suitable means, to update the medical or non-medical information stored on personal medical information storage device 300 and/or remote medical information storage device 200.

Personal medical information storage device 300 may also comprise a forms module configured to store, track, and update provider forms. In one embodiment, personal medical information storage device 300 may come pre-loaded with at least one provider-specific form. For instance, personal medical information storage device 300 may be offered by a provider and may already include that provider's relevant forms. In one embodiment, the form module may include an intake form, a follow-up form, and HIPAA-related forms, among other things. The forms module may also be configured to establish a communications link with a remote server and update any forms stored in the forms module. In one embodiment, the forms module may be configured to automatically fill portions of the forms loaded therein based on a user's medical and non-medical information. Of course, the preceding examples are merely provided for illustration and are not to be taken in a limiting sense.

FIGS. 4a and 4b illustrate a personal medical information storage device 400. In one embodiment, personal medical information storage device 400 comprises an interface connection 405 and a wearable band 410. As used herein, wearable refers to anything that may render personal medical information storage device 400 suitable to be worn, or secure to a user, such as a band, a clasp, a clip, a bracelet, or a chain, among other things. Interface connection 405 may provide access to a computer readable storage medium on which a plurality of modules may be stored. In one embodiment, interface connection 405 may be a USB or mini-USB plug. Alternatively, interface connection 405 may be any form of interface configured to give client device 125a access to the computer readable storage medium of the personal information storage device 400. For instance, in one embodiment, interface connection 405 may be a SD card, a USB thumb drive, or a mini-USB thumb drive.

Interface connection 405 may be completely removable from wearable band 410, or may be integrated therein and may be accessible by moving a portion of wearable band 410. For instance, in one embodiment, wearable band 410 may be a hard rubber band configured to snap out of place and reveal a USB plug (interface connection 405), and then snap back into place after use.

FIGS. 5a and 5b show a personal medical information storage device 500 comprising an interface connection that may be hidden (505b) or exposed (505a) by removing interface connection 505b from wearable band 510. In one embodiment, a clasp 515 may hold a computer readable storage medium comprising an interface connection (505a or 505b), and the clasp may be slidably removable from wearable band 510. For instance, personal medical information may be stored on a computer readable storage medium, such as an SD card, and held in place within a wearable band 510 by a clasp 515. For example, a first responder arriving at the scene of an accident may identify the personal medical information storage device 500 on an accident victim, may remove interface connection 505b to access the accident victim's vital information and facilitate the care of the patient.

Figure 6A:
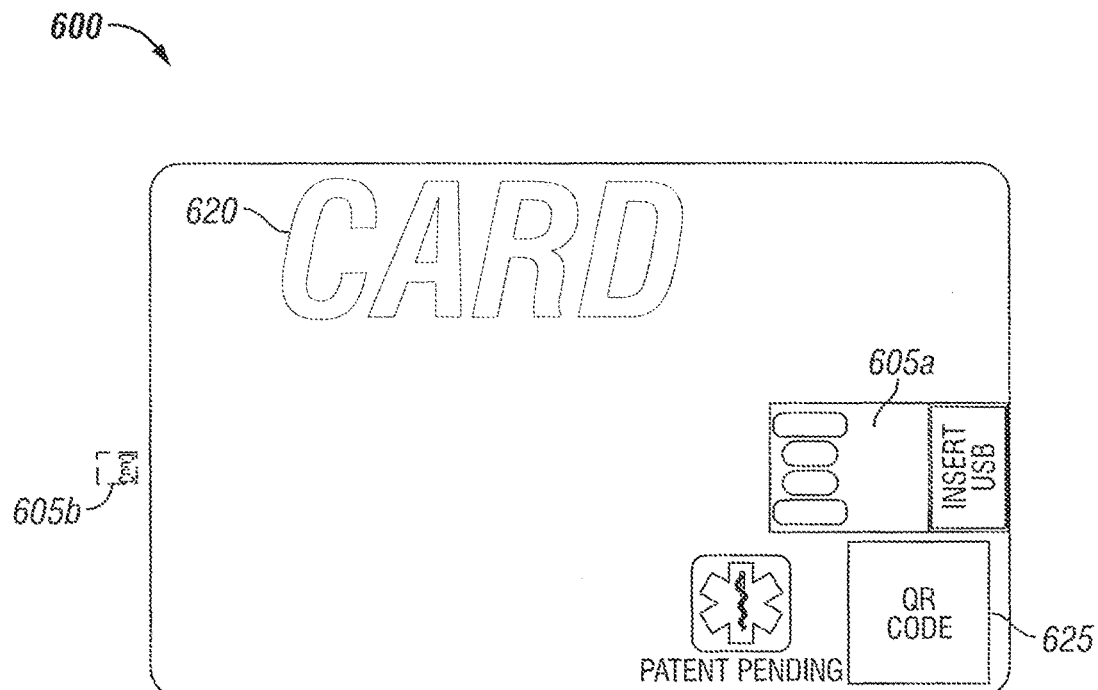
FIGS. 6a and 6b are an illustration of yet another personal medical information storage device.
Figure 6B:
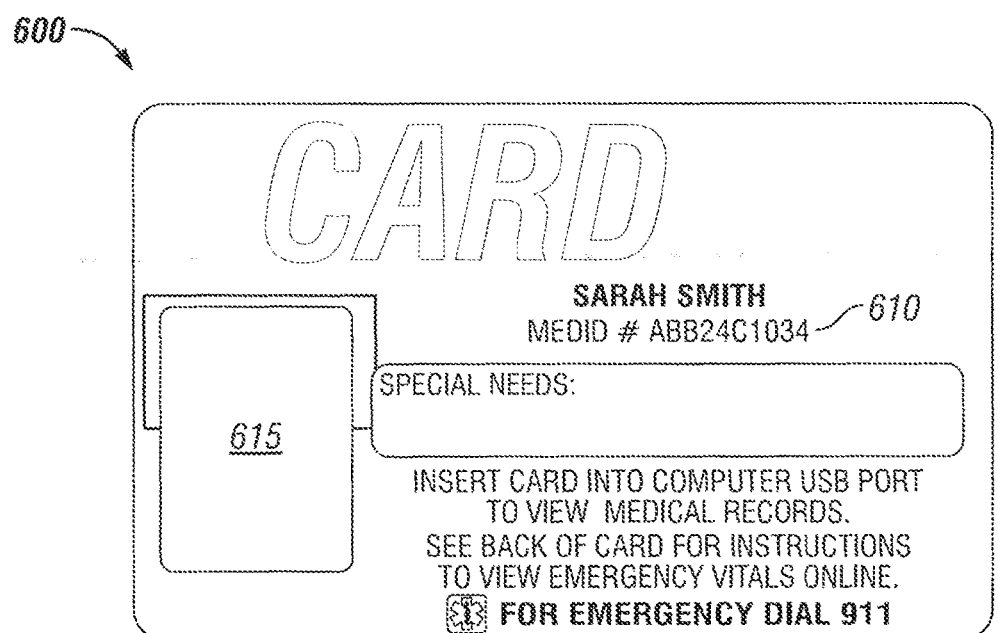

FIGS. 6a and 6b show a card embodiment of a personal medical information storage device 600. In this card embodiment, personal medical information storage device 600 comprises an interface connection 605a, which may be a credit card-like IC chip (such as the EMV chips used in charge cards) and display a user name 610. Optionally, personal medical information storage device 600 may also include a mini-USB connection 605b, a user photo 615, a logo 620, and/or a QR code 625.

In operation, mini-USB connection 605b may enable connection with client devices 125c and 125d, which commonly do not have full-sized USB plugs. Additionally, a QR code 625 may enable a person, such as an emergency responder, to scan the card and have immediate access to the user's basic information, without having to try and create a connection with personal medical information storage device 600. In one embodiment, the inclusion of user photo 615 facilitates a visual confirmation that the personal medical information storage device 600 belongs to the user.

It is understood that personal medical information storage device 600 (in any embodiment) may comprise other modules and/or functionality including, but not limited to, GPS, RFID, and NFC. For instance, in one embodiment, a GPS chip (not shown) may facilitate geospatial identification for authorization purposes. In another embodiment, the GPS chip may be configured to provide relevant information to facilitate the identification of relevant advertisements. Of course, a GPS chip may be configured to provide any number of relevant functionalities and uses to a personal medical information storage device 600. In other embodiments, radio-based close proximity transmission features and functionality may also be included. For instance, personal medical information storage device 600 may include RFID or NFC functionality in order to facilitate data transmission. Of course the preceding examples are intended to illustrate the breadth of functionality envisioned by the current disclosure, and are not to be taken in a limiting sense.

FIG. 7 illustrates one method 700 of using a personal medical information device (for the purpose of the method figures, personal medical information device 400 and client device 125a will be referred to in a non-limiting sense). In a first method step 705, a personal medical information device 400 is read. For instance, personal medical information device 400 may be inserted into a client device 125a. In another embodiment, personal medical device 400 may be read using a QR code 625. Generally speaking, reading a device refers to any method or step comprising accessing data or a file stored on a computer readable storage medium.

In a next method step 710, personal medical information device 400 is authenticated to confirm that it has been reported neither lost nor stolen. For instance, in one embodiment, after personal medical information device 400 is connected into a client device 125a, a routine may automatically run to determine whether the personal medical information device 400 has been reported stolen. In other embodiments, GPS or biometrics may be relied upon to determine identity based on a combination of location and biological identification characteristics (such as fingerprints).

To the extent that personal medical information device 400 does not properly authenticate, a wipe (or data erasure)

step 715 may be run to protect the data stored thereon. In one embodiment, if the authentication routine receives a response indicating that the personal medical information device 400 has been reported lost or stolen, the routine may then automatically launch a data shredding or reformatting routine to completely and securely erase or wipe all of the information stored on the personal medical information storage device 400.

However, to the extent that the personal medical information storage device 400 authenticates properly, a next method step 720 comprises presenting basic information to the user. For example, once the personal medical information storage device 400 properly authenticates, the screen of client device 125a may display basic vital information including, but not limited to, a medication log, allergies, vital statistics (date of birth, gender, blood type, weight and height, etc.), address, and emergency contacts, among other things. In another embodiment, detailed information may be password-protected.

Therefore, in a subsequent optional method step 725, the user is prompted with a password request in order to access detailed medical information. In one embodiment, certain tabs and portions of the UI may comprise lock icons suggesting the need to enter a password to access those particular areas of the personal medical information storage device 400. Once those tabs or icons are selected, the user may be prompted to enter a password. If the password does not match, then the user may be taken back to the default page. Of course, a lock icon is not required and may be provided for the user's benefit.

However, in one embodiment, if the password matches, a next method step 730 is launched by which private or protected information is presented to the user via client device 125a. For instance, if the user seeks to access a portion of personal medical information device 400 where sensitive financial documents are stored, and the user correctly enters the password, then the user may next be taken to a screen where the sensitive information is presented. Otherwise, the user may be taken back to the default screen.

FIG. 8 illustrates a method 800 of authenticating a device. In a first method step 805, an autorun routine may launch automatically once a personal medical information storage device 400 is connected to a client device 125a. In a next method step 810, the routine may attempt to determine whether or not client device 125a has a connection to a network interface server 115 that may be used for the authentication process. In one embodiment, the connection may comprise a connection to the Internet. However, the connection may be any connection, be it local or remote, that allows the routine to access a database (e.g., 120) containing authorization information. If the routine determines that there is no remote connection, then the routine may only authorize access to basic medical information (see method step 815).

If the routine determines that there is a connection to a network interface server 115, then a next method step 820 may comprise querying the network interface server 115 to determine whether the personal medical information device 400 has been reported lost or stolen. In one embodiment, this step may comprise transmitting a unique device-specific identification number and cross-referencing that number with a report of devices that have been reported either lost or stolen. However, the authentication step may also be accomplished based on a user name, among other things, associated with a personal medical information device 400.

If it is determined that the personal medical information device 400 has not been reported lost or stolen, then the routine may send an authorization command to the client device 125a to authorize access to the data contained thereon (see step 830). However, to the extent that the personal medical information device 400 has been reported either lost or stolen, the authorization routine may launch a wipe or erasure instruction to completely erase the data stored thereon. For instance, the personal medical information storage device may automatically perform a reformatting operation to completely and securely erase all sensitive information.

Figure 9:
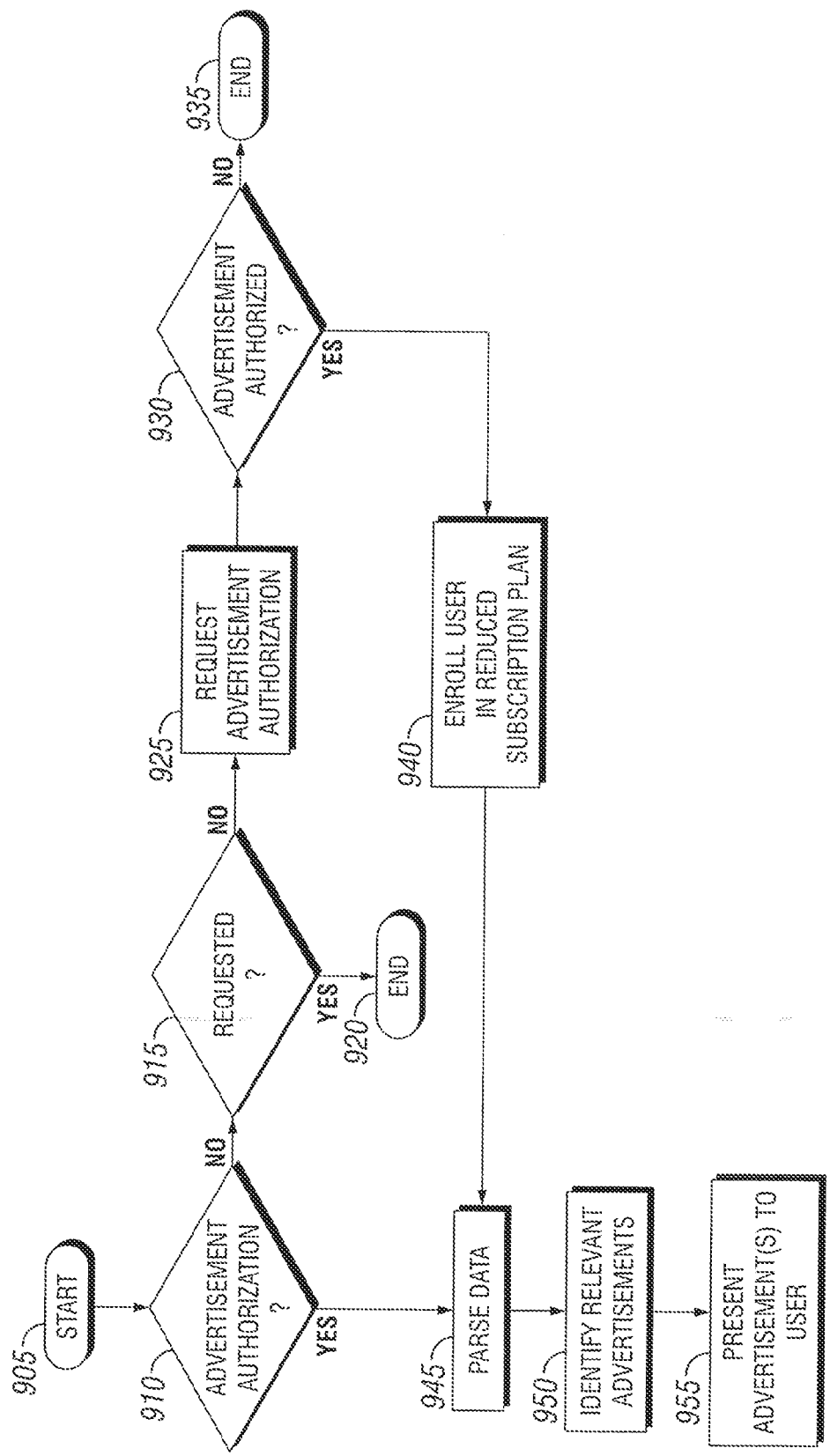
FIG. 9 illustrates a method of receiving authorization for an advertisement-subsidized service plan of a personal medical information storage device.

FIG. 9 illustrates a method 900 of providing targeted advertising to a user in the form of, for instance, an advertisement-subsidized service plan. In a first method step 905, an advertisement authorization routine (such as a script) is run. In a next method step 910, the authorization routine determines whether a given user has authorized targeted advertising. In one embodiment, when a user signs up with a personal medical information storage system 100, the user may accept an agreement to receive a device without a monthly subscription (or with a reduced subscription) in exchange for receiving targeted advertising based on the user's particular medical information. If the user does authorize targeted advertising, an advertisement authorization flag may be set indicating this authorization. Of course, any other suitable process may be used to detect authorization.

To the extent that authorization for targeted advertisement has not been set, then a related routine may be run to detect whether the user will authorize the advertising module to use personal information. For instance, in method step 915 the system ascertains whether a request for targeted advertisements has been made. In one embodiment, method step 915 may comprise first determining whether the particular user has already been asked to authorize targeted advertising (via, for example, a flag or variable). If the user already has been asked and has not authorized advertising, then the advertising routine may terminate 920.

However, to the extent that advertising authorization has not been requested, then the request may be made in a subsequent method step 925. For instance, the user may be prompted, via client device 125a to approve targeted advertising (or to opt out). If the user does not authorize targeted advertising, then the routine may end 935. But if the user does authorize targeted advertising, then the user may be automatically enrolled in a reduced cost or subscription free service plan 940.

Once it is determined that the user has authorized a reduced subscription service plan, then a next method step 945 may comprise parsing the user's information to identify potentially relevant advertising. For instance, in one embodiment, the advertisement module 220 may scan the different entries in the personal medical information storage device 400 and categorize entries by type, such as medications, allergies, chronic conditions, locality, etc. The advertisement module 220 may then compare that information with a list of relevant advertisements that may also be categorized. In another embodiment, advertisement module 220 may refer to a finite number of potential advertisements, categorized by type, and compare the advertisements with user data to identify potentially relevant advertisements.

Finally, once relevant advertisements have been identified, a final method step 955 comprises presenting the relevant advertisements to the user. For instance, if the user is diabetic and advertisement module 220 identifies that the user is diabetic, then the advertisement module may send an advertisement, such as a video, to client device 125a to enable the user to find out about a potentially relevant product. In another embodiment, once a relevant match is identified, an advertisement may be sent to the user via other means, such as a telephone call, mail, or any other means.

Figure 10:
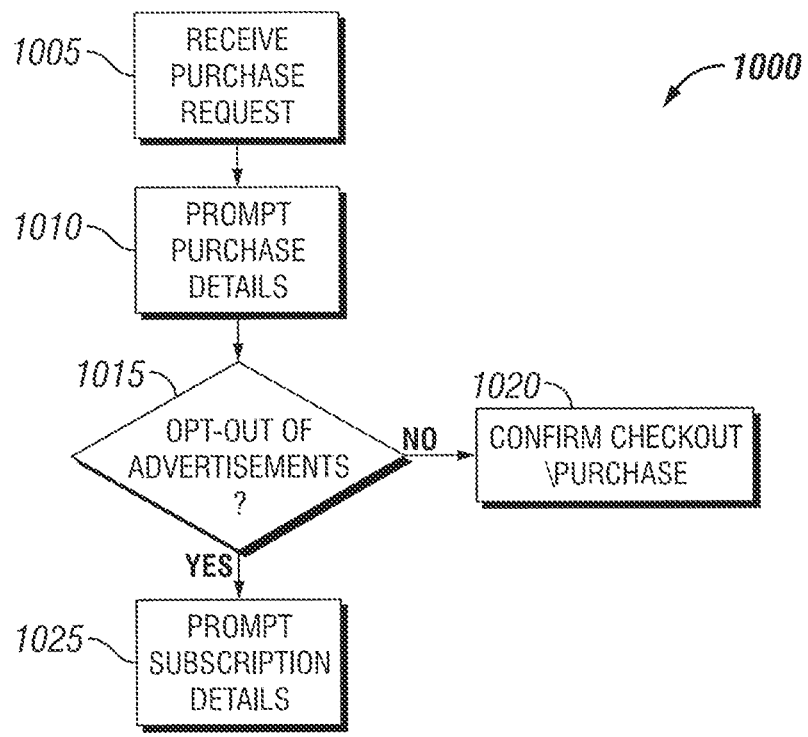
FIG. 10 illustrates a method of receiving an opt-out request for an advertisement-subsidized service plan of a personal medical information storage device.

FIG. 10 illustrates a method of prompting a user to enroll in a reduced subscription targeted advertisement plan 1000. In a first method step, a network interface server 115 receives a request to purchase a personal medical information storage device 400. This may be, for example, via a website, over the phone, or any other suitable means of purchasing and receiving a request to purchase a device. In a next method step 1010, network interface server 115 prompts the entry of purchase details. For example, the user may be presented with a web page displaying address and payment information, among other things.

Network interface server 115 may request that the user opt out of targeted advertising based on the user's personal medical information (see step 1015). In one embodiment, the opt out may occur on the purchase page via a check box. Alternatively, the opt out may be requested in a preceding or subsequent page. If the user elects to opt out of the targeted advertising subscription plan, then a next step 1025 may comprise prompting the entry of subscription details. For example, if the user checks the box opting out of the reduced cost subscription plan, then the user may be presented with a new payment page requesting the entry of payment information for a regular subscription and authorization to charge the user on a regular basis therefor. As used herein, a reduced cost subscription plan may be any service plan comprising a reduction in overall cost of the plan, and may include a free service at one extreme, and slight reduction at the other extreme. In one embodiment, a reduced cost subscription plan may comprise a full cost subscription plan in conjunction with a service credit. For instance, a user may receive an incremental reduction in subscription cost based upon, inter alia, the frequency of advertisements received and/or viewed.

However, if, on the other hand, the user does not opt out of the reduced subscription plan, then the purchase of the personal medical information storage device 400 may be purchased after confirming the purchase information and/or checking out (see step 1020).

Figure 11:
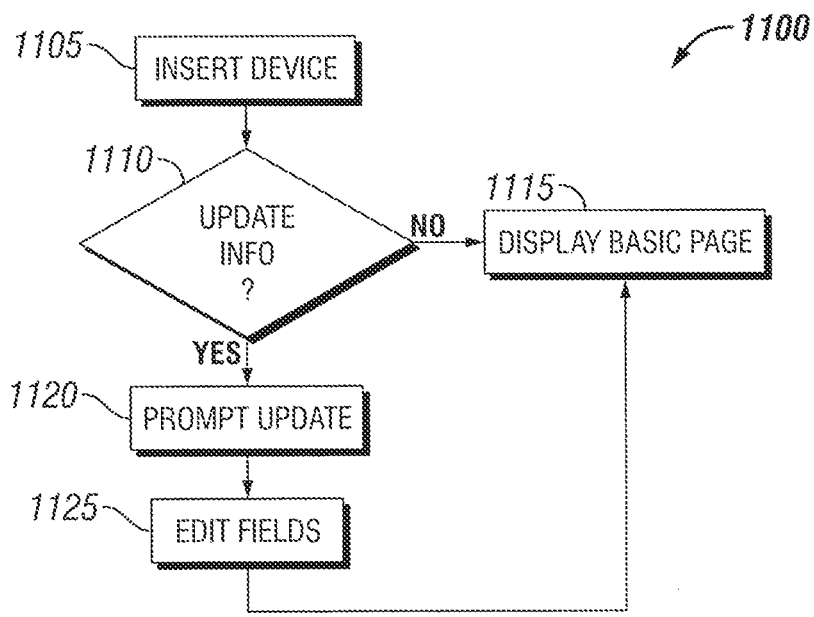
FIG. 11 illustrates a method of prompting a user to update the personal medical and non-medical information of a personal medical information storage device.

FIG. 11 illustrates a method of prompting a user to update his or her medical and non-medical information in a personal medical information storage system 100. In a first method step 1105, a user connects a personal medical information storage device 400 into a client device 125a to initiate an update script. In a next method step 1110, the update routine queries whether a triggering event has occurred that would lead to a request to update information. For example, triggering events may be the simple passage of time since the last information update, a request by a service provider, or a schedule an appointment, among other things. If the routine determines that a triggering event has occurred, then the user is prompted to update his or her personal information (see step 1120). If not, however, then the client device 125a displays the default page (see step 1115).

If an update is requested, the request may come in the form of a pop-up window, email reminders, a telephone call, or any other suitable reminder. In one embodiment, the user may be prompted to update information via a pop-up window containing a link to an "edit fields" window configured to facilitate data entry. Once edits are entered, then they may be saved both locally on a personal medical information storage device 400 and remotely in a database 120.

Figure 12:
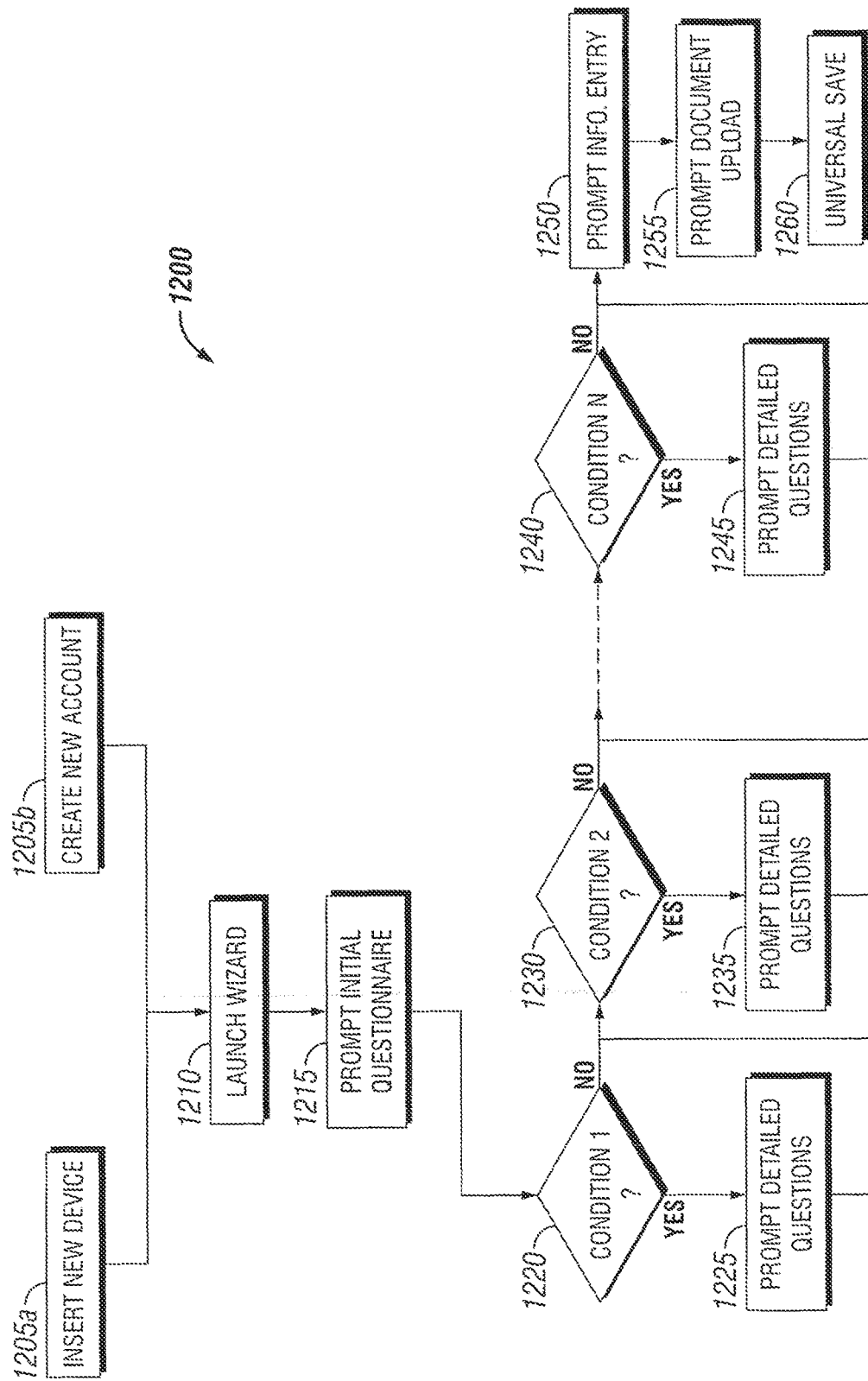
FIG. 12 illustrates a method of prompting data entry for a personal medical information storage device.

FIG. 12 illustrates a method of efficiently collecting information from a user. In computer parlance, such information requests and user interactions are often accomplished by a wizard, or targeted data entry as guided by the client device 125a, personal medical information storage device 400, and/or remote medical information storage device 200.

The data entry wizard may be encountered at at least one of two situations: first, when a new personal medical information storage device 400 is inserted into a client device 125a for the first time; second, when a new account is created on-line (usually in conjunction with the purchase of a personal medical information storage device 400). Thus, method 1200 may commence with either method step 1205a or 1205b. Preferably, when a user purchases a new personal medical information storage device 400 on-line, and then enters personal information in conjunction with the purchase and account creation, that personal information may be automatically stored upon the personal medical information storage device 400 upon delivery (or alternatively, automatically once the device is plugged into a client device for the first time).

In a first method step 1210, a wizard module is launched to guide the user through the data entry process. For example, the wizard may be through a series of pop-up windows and questions on client device 125a. In another embodiment, the "wizard" may consist of a guided telephone call (either with a recorded operator, or with a live operator). In a subsequent method step 1215, the user is presented with an initial questionnaire in order to target the questions asked by the wizard and target relevant information (and therefore eliminate wasted response time). Thus, for example, a next step 1220 may comprise requesting that the user identify whether or not he or she has a first condition (e.g., diabetes). If the user answers in the affirmative, then the wizard may next prompt more detailed questions (see step 1225) in order to fully populate the fields corresponding to the first condition. Otherwise, the user may be prompted to answer a question regarding a second condition (see step 1230). Yet again, if the user answers affirmatively regarding the second condition, then the wizard may prompt more detailed information regarding that condition (see step 1235). Otherwise, the wizard may prompt responses related to other conditions. Any number of possible conditions are contemplated by the present disclosure, but for the purposes of brevity and avoiding unnecessary repetition, the next step in the method 1200 comprises prompting the user to answer a question as to an n condition (see step 1240). Again, if the user answers in the affirmative as to the nth condition, then the wizard will prompt questions to fill out information related to the nth condition (see step 1245). Otherwise, the wizard may continue on to the next method step. Of course, the above illustration is merely one example of the wizard concept and should not be taken in a limiting sense.

Once the wizard has completed its initial battery of questions, the user may then be prompted to enter information as desired (see step 1250). For example, the user may desire to enter health insurance information that may not be required by the wizard, but that the user may deem to be useful. Personal medical information storage device 400 may be configured to store any amount of possible medical and non-medical information thereon. For instance, in an additional method step 1255, the user may elect to store documents to personal medical information storage device 400. In one embodiment, the documents may include birth certificates, marriage certificates, living wills, and X-rays among other things.

Finally, the wizard may prompt the user to save all of the information entered in a last method step 1260.

Figure 13:
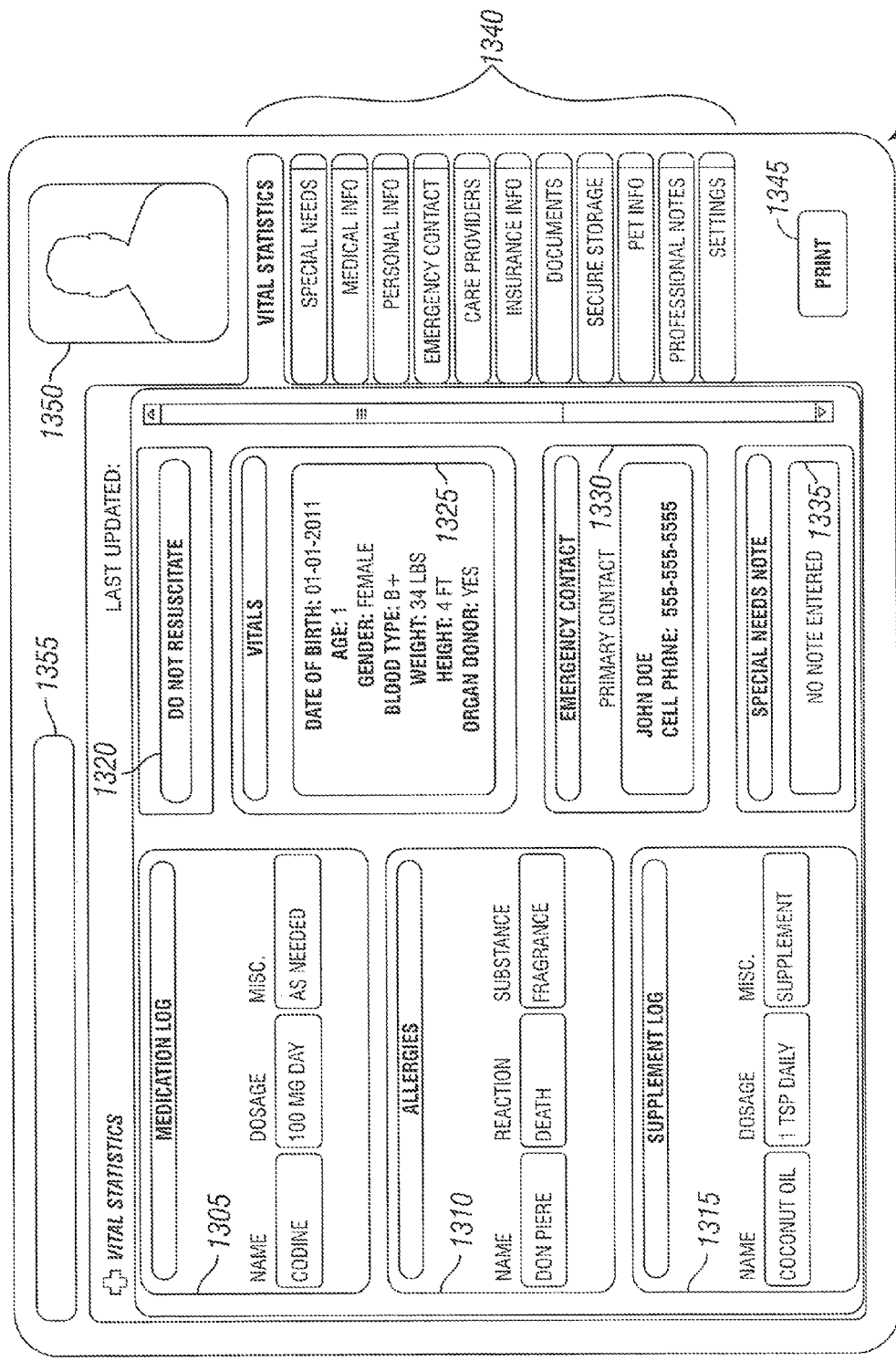
FIG. 13 is an example of a screen shot presenting basic personal medical information.

FIG. 13 illustrates one embodiment of a default first page 1300 of a personal medical information storage device 400 as displayed on a client device 125a. For instance, the default first page 1300 may comprise a logo 1355, any number of potential information such as, a medication log 1305, an allergies log 1310, a supplement log 1315, emergency responder targeted notes, such as a "do not resuscitate" note 1320, a vitals log 1325, an emergency contact log 1330, and a special needs notes 1335. The default first page 1300 may also comprise a print button 1345. In one embodiment, the default first page comprises a list of tabs 1340, that may be used to organize information much like medical folders. Default first page 1300 may also include a photo identification 1350 in order to facilitate identification. In practice, any other information that may be important for, for example, first responders, may be included on the default first page 1300.

Figure 14:
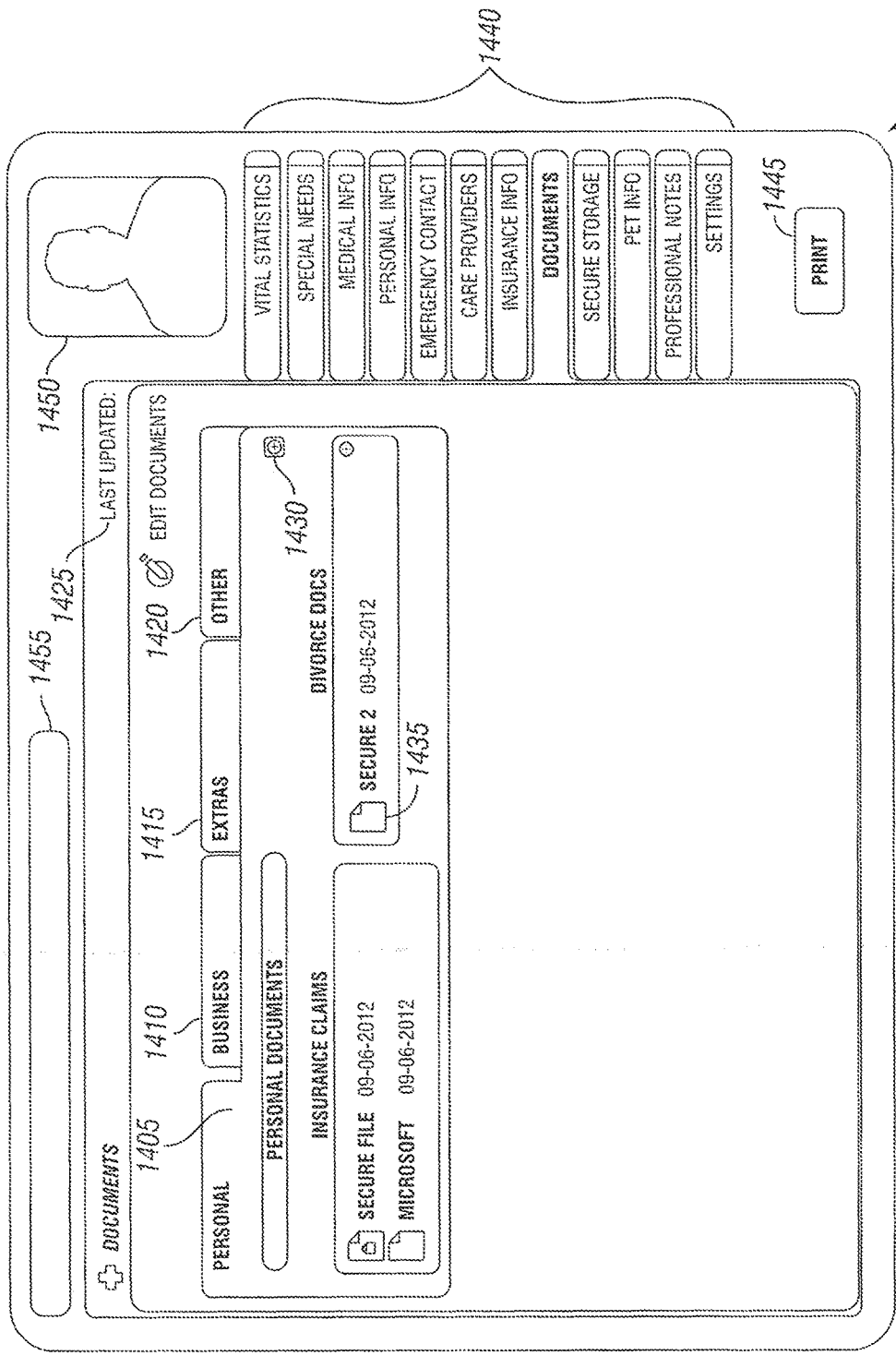
FIG. 14 is an example of a screen shot presenting documents saved to a personal medical information storage system.
Figure 16:
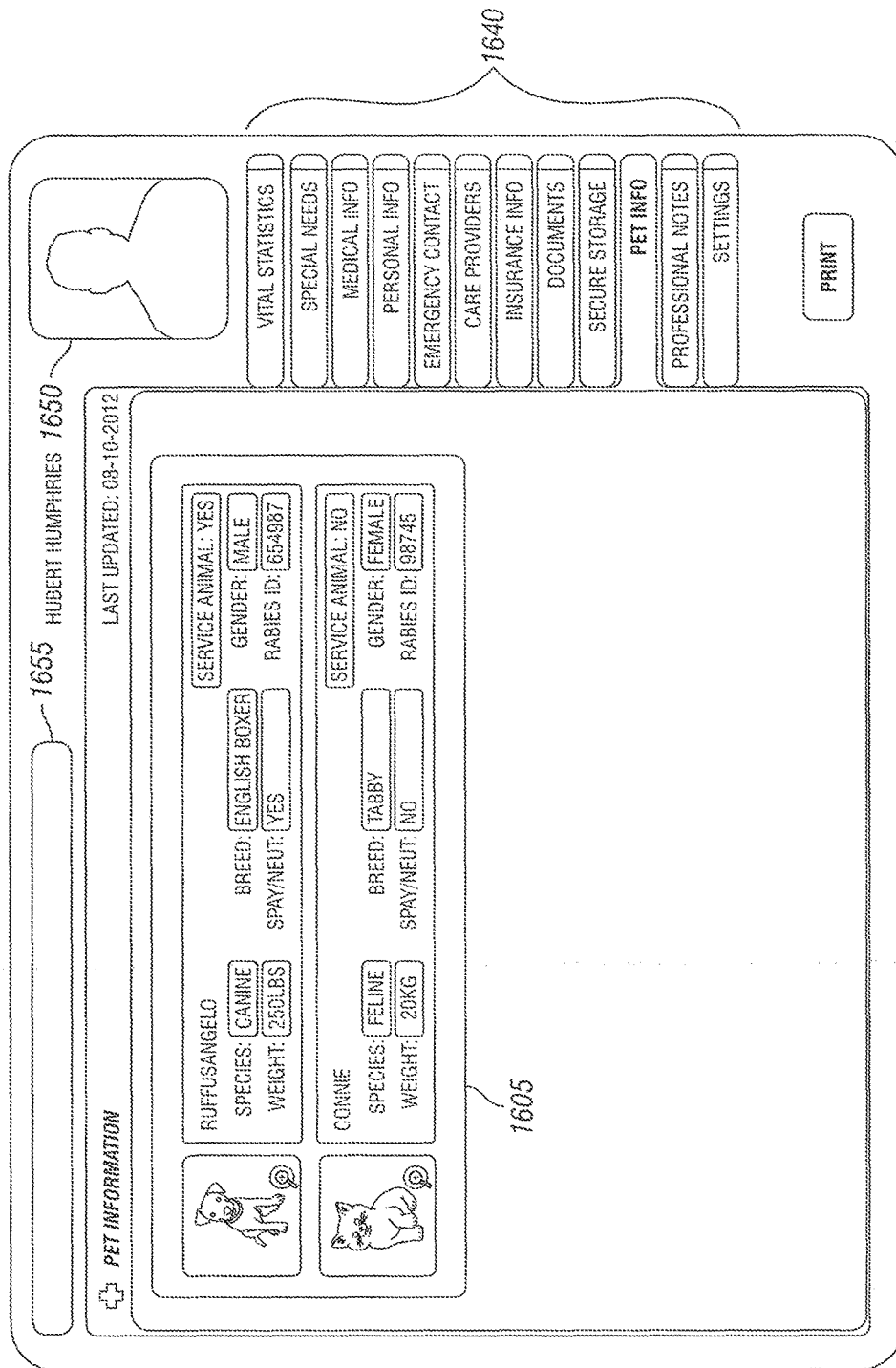
FIG. 16 is an example of a screen shot presenting pet or animal information.

FIG. 14 illustrates one embodiment of a documents screen 1400 of the present disclosure. The documents screen 1400 may comprise a logo 1455 that may be customized for a service provider, or may indicate the manufacturer of the personal medical information storage device 400. The documents screen 1400 may be organized by the document type. For example, documents screen 1400 may comprise categories for personal documents 1405, business documents 1410, extras 1415, and other documents 1420. Additionally, any other number of relevant document categories and classifications may be used as relevant. The documents may be protected by a password, and an icon 1435 may indicate that a given document may only be accessed by entering a password. Documents screen 1400 may also comprise an add button 1430 to facilitate the addition of new documents.

Figure 15:
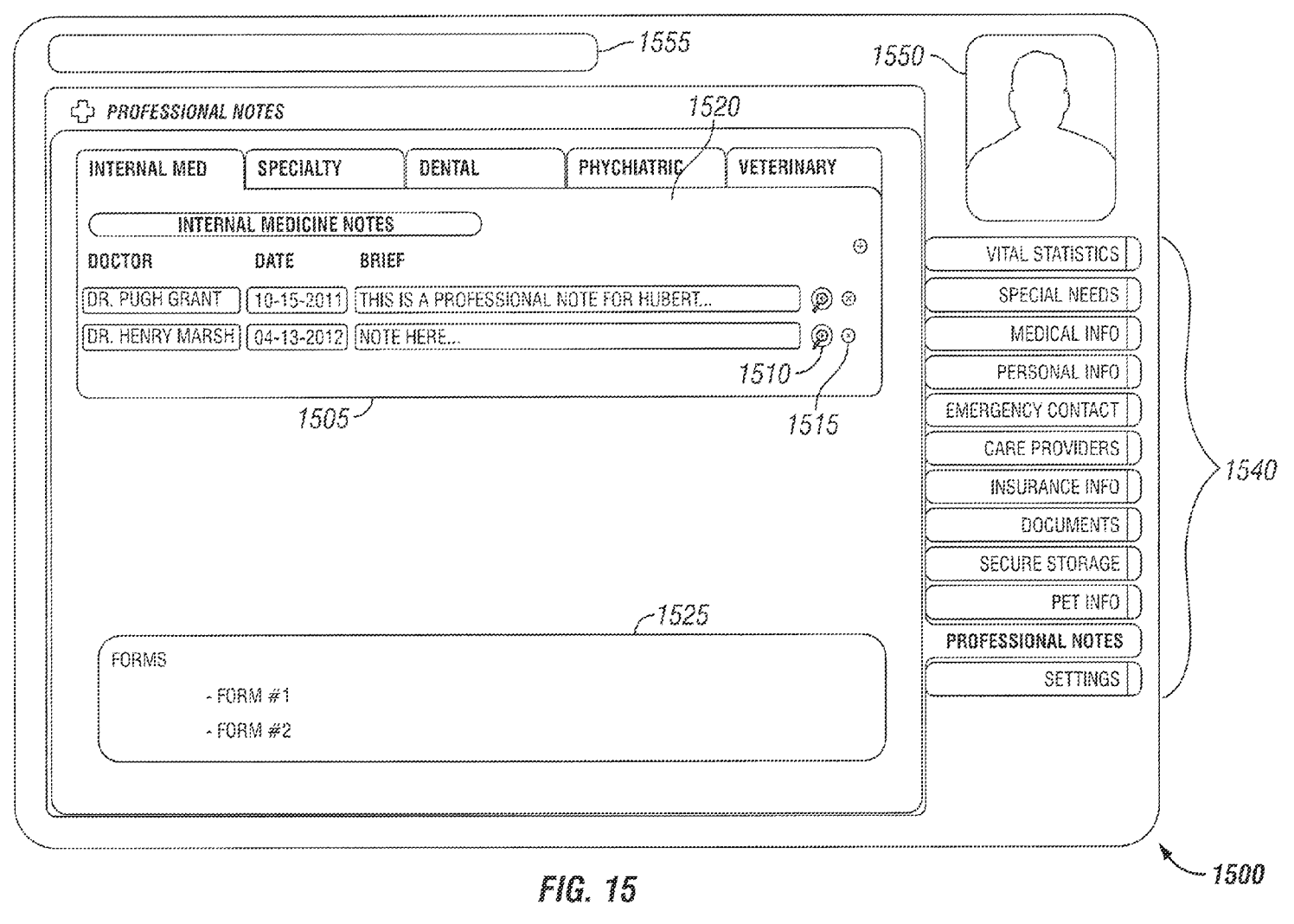

FIG. 15 illustrates a physician notes screen 1500 according to one embodiment. The physician notes screen 1500 may comprise categorized physician notes grouped by tabs 1505. Alternatively, any suitable form of categorization may be employed. In one embodiment, once physician notes are created and saved, they may not be edited. In this embodiment, the notes may only viewed by clicking on a view button 1510 or deleted by clicking on a delete button 1515. Additionally, physician notes screen 1500 may comprise a form field 1525 containing relevant forms that the patient may fill out in advance of an appointment. In one embodiment, the forms may be automatically populated based on information in the personal medical information storage system 100. For example, prior to an appointment, a user may be prompted to download, fill out, and bring a given form to the appointment. The form may be pre-loaded on a personal medical information storage device 400, and when the user opens the form, certain fields may be automatically filled requiring the user to only fill in a limited number of fields prior to his or her appointment.

In a pet/animal information screen 1600, information pertaining to a pet or animal may be stored on a personal medical information storage device 400. In one embodiment, the pet/animal information may be stored on a pet owner's personal medical information storage device 400. In another embodiment, pet/animal information may be stored in a personal medical information storage system 400 stored, for instance, in an animal collar, among other things. The pet/animal information screen 1600 may comprise a pet/animal data section configured to store information related to the pet or animal in question. Relevant information may include the species, breed, gender, weight, and vaccination records, among other things.

Although this invention has been described in terms of certain preferred embodiments, other embodiments that are apparent to those of ordinary skill in the art, including embodiments that do not provide all of the features and advantages set forth herein, are also within the scope of this invention. Accordingly, the scope of the present invention is defined only by reference to the appended claims and equivalents thereof.

What is claimed is:

1. A subscription-based personal medical information storage device comprising:
  a data storage unit comprising a computer readable storage medium configured to:
    store medical and non-medical information of a user; and
    facilitate the retrieval of medical and non-medical information of the user from a remote medical information storage device;
  wherein the data storage unit is configured to be read by a general purpose computing device, and wherein the data storage unit is configured to automatically run an authentication routine upon connection with the general purpose computing device to determine whether or not the personal medical information storage device is lost or stolen, wherein the authentication routine is configured to:
    transmit a unique device-specific identification corresponding to the subscription-based personal medical information storage device to the remote medical information storage device, wherein the remote medical information storage device maintains a database indicating device-specific identifications associated with devices that have been reported lost or stolen;
    receive data, directly at the authentication routine from the remote medical information storage device, indicating whether the subscription-based personal medical information storage device associated with the transmitted unique device-specific identification has been reported lost or stolen;
    if, and only after, the authentication routine determines the received data confirms that the personal medical information storage device is neither lost nor stolen, prompt the user to enter a password and authenticate the password of the user to grant access to the medical and non-medical information stored in the data storage unit; and
    if the authentication routine determines the received data indicates that the personal medical information storage device is reported as lost or stolen, without user input or prompting the user to enter the password, deny access to and automatically erase the medical and non-medical information stored in the data storage unit;
  the data storage unit further comprising:
    a communication module configured to facilitate a communication connection with the remote medical information storage device, and wherein the remote medical information storage device comprises a processor configured to:
      prompt a user for authorization to parse the medical information of the user to provide personalized advertisements and recommendations in exchange for a reduced cost subscription plan,
      upon reception of user authorization, parse the medical information of the user to facilitate the identification of relevant advertisements,
      present the user with at least one relevant advertisement, and
      offer a reduced cost subscription plan or service credit to the user.

2. The subscription-based personal medical information storage device of claim 1, wherein the data storage unit is further configured to detect a triggering event, in response to the triggering event, transmit an update prompt configured to request the user to input updated information, save updated information to the data storage unit, and transmit the updated information to the remote medical information storage device for remote storage.

3. The subscription-based personal medical information storage device of claim 2, wherein the triggering event comprises at least one of:
a predetermined passage of time since a previous date of data entry;
a request from a service provider; and
a scheduled appointment with a service provider.

4. The subscription-based personal medical information storage device of claim 1, further comprising a wizard configured to present a user with an initial questionnaire regarding a predetermined number of conditions, receive responses from the user identifying whether the user has any of the predetermined number of conditions, and prompt user with additional questions for any of the predetermined number of conditions for which the user answered in the affirmative.

5. The subscription-based personal medical information storage device of claim 1, further comprising a physician notes module configured to, when implemented by a processor, store physician notes and files, encrypt physician notes and files, and grant access to physician notes and files only upon successfully entering the password.

6. The subscription-based personal medical information storage device of claim 5, wherein the physician notes module is configured to, when implemented by the processor, restrict access to physician notes and files to read-only access and delete-only access.

7. The subscription-based personal medical information storage device of claim 1, further comprising a pet/animal module configured to store pet information including pet species and pet vaccination records.

8. The subscription-based personal medical information storage device of claim 1, further comprising a forms module configured to, when implemented by a processor, store provider forms, and wherein the provider forms are pre-loaded on the subscription-based personal medical information storage device.

9. The subscription-based personal medical information storage device of claim 1, further comprising a wearable band configured to secure the subscription-based personal medical information storage device to a user.

10. A medical information storage system comprising:
a medical information storage server comprising a processor, the medical information storage server configured to store medical and non-medical information from users of the medical information storage system, wherein the medical information storage server maintains a database indicating device-specific identifications associated with devices that have been reported lost or stolen;
a personal medical information storage device configured to exchange information with the medical information storage server and to store medical and nonmedical information in a computer readable storage medium, wherein the personal medical information storage device is configured to automatically run an authentication routine upon connection with the general purpose computing device to determine whether or not the personal medical information storage device is lost or stolen, wherein the authentication routine is configured to:
transmit a unique device-specific identification corresponding to the personal medical information storage device to the medical information storage server;
receive data, directly at the authentication routine from the medical information storage server, indicating whether the personal medical information storage device associated with the transmitted unique device-specific identification has been reported lost or stolen;
if, and only after, the authentication routine determines the received data confirms that the personal medical information storage device is neither lost nor stolen, prompt the user to enter a password and authenticate the password of the user to grant access to the medical and non-medical information stored in the data storage unit; and
if the authentication routine determines the received data indicates that the personal medical information storage device is reported as lost or stolen, without user input or prompting the user to enter the password, deny access to and automatically erase the medical and non-medical information stored in the data storage unit;
an advertisement module, implemented at least in part by the processor of the medical information storage server, configured to parse medical and non-medical information stored on the medical information storage server and the personal medical information storage device, and to facilitate the identification of at least one relevant advertisement or recommendation for the user based upon the medical and non-medical information of the user; and
a communication module configured to communicate the at least one relevant advertisement or recommendation to the user.

11. The medical information storage system of claim 10, wherein the communication module is configured to prompt the user for authorization to parse medical and non-medical information of the user, and wherein if the user does not provide authorization therefor, the user is prompted to sign up for a subscription service.

12. The medical information storage system of claim 10, wherein the advertisement module is configured to detect whether the user has a condition including at least one of diabetes, high blood pressure, or depression, and present the user with a relevant product, treatment, or recommendation.

13. The medical information storage system of claim 10, further comprising a forms module configured to, when implemented by a processor, store, receive, and transmit provider forms to or from the personal medical information storage device.

14. The medical information storage system of claim 13, wherein the provider forms are pre-loaded on the personal medical information storage device.

15. The medical information storage system of claim 10, further comprising a physician notes module configured to, when implemented by the processor, store physician notes and files, secure physician notes and files with the password, and restrict access to physician notes and files to read-only access and delete-only access.

16. The medical information storage system of claim 10, further comprising a sport module configured to, when implemented by a processor, store sports information to the personal medical information storage device, and where the sports information comprises exercise routine data, performance histories, distance travelled, and goals.

17. A personal medical information storage device comprising:
- a computer readable storage medium configured to store both medical and nonmedical information;
- an authentication module stored on the computer readable storage medium, the authentication module configured to, when executed by a processor, automatically run an authentication routine upon connection with the general purpose computing device to determine whether or not the personal medical information storage device is lost or stolen, wherein the authentication routine is configured to:
  - transmit a unique device-specific identification corresponding to the personal medical information storage device to a remote medical information storage server, wherein the remote medical information storage server maintains a database indicating device-specific identifications associated with devices that have been reported lost or stolen;
  - receive data, directly at the authentication routine from the remote medical information storage server, indicating whether the personal medical information storage device associated with the transmitted unique device-specific identification has been reported lost or stolen;
  - if, and only after, the authentication routine determines the received data confirms that the personal medical information storage device is neither lost nor stolen, prompt the user to enter a password and authenticate the password of the user to grant access to the medical and non-medical information stored in the data storage unit; and
  - if the authentication routine determines the received data indicates that the personal medical information storage device is reported as lost or stolen, without user input or prompting the user to enter the password, deny access to and automatically erase the medical and non-medical information stored in the data storage unit; and
- a physician note module stored on the computer readable storage medium and comprising:
  - an encrypted physician notes field;
  - an encrypted physician files field for images and PDFs;
  - a save functionality configured to, when implemented by the processor, restrict access to the encrypted physician notes field and the encrypted physician files field to read-only access and delete-only access; and
  - a form module configured to, when implemented by the processor, store a plurality of doctor-specific forms for downloading on a general purpose computing device.

* * * * *